United States Patent [19]

Kuwada et al.

[11] 4,017,620
[45] Apr. 12, 1977

[54] THIENODIAZEPINE DERIVATIVES

[75] Inventors: Yutaka Kuwada, Ashiya; Kanji Meguro, Takarazuka; Hiroyuki Tawada; Takashi Sohda, both of Takatsuki; Hideaki Natsugari, Nishinomiya; Yoshiaki Sato, Kobe, all of Japan

[73] Assignee: Takeda Chemical Industries, Ltd., Osaka, Japan

[22] Filed: May 8, 1975

[21] Appl. No.: 575,727

[30] Foreign Application Priority Data

May 13, 1974 Japan .................. 49-53747

[52] U.S. Cl. .................. 424/248.51; 260/247.1 L; 260/268 PC; 260/268 TR; 260/293.57; 260/308 R; 260/332.2 A; 424/250; 424/267; 424/269
[51] Int. Cl.[2] ........................ C07D 495/14
[58] Field of Search ... 260/293.57, 308 R, 247.1 L, 260/268 PC, 268 TR, 293.59; 424/267, 269, 248, 250

[56] References Cited

UNITED STATES PATENTS

| | | |
|---|---|---|
| 3,784,556 | 1/1974 | Gagneux et al. .............. 260/308 R |
| 3,862,171 | 1/1975 | Gagneux et al. .............. 260/308 R |
| 3,870,714 | 3/1975 | Gagneux et al. .......... 260/247.5 EP |

FOREIGN PATENTS OR APPLICATIONS

| | | |
|---|---|---|
| 6,916,543 | 5/1970 | Netherlands |
| 2,229,845 | 12/1972 | Germany |

*Primary Examiner*—G. Thomas Todd
*Attorney, Agent, or Firm*—Burgess Ryan and Wayne

[57] ABSTRACT

There is disclosed new thienodiazepine derivatives of the general formula:

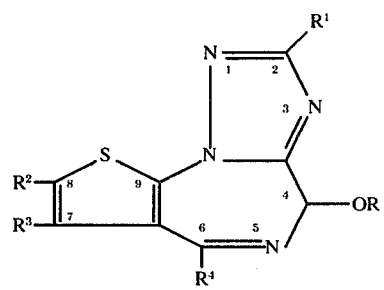

wherein $R^1$ represents a carboxyl group which may be esterified or amidated; each of $R^2$ and $R^3$ represents hydrogen atom or a lower alkyl group, or $R^2$ and $R^3$ may bond to each other to form an alkylene group; $R^4$ represents a phenyl group which may have substituent; and R represents hydrogen atom, an acyl group or an alkyl group, or its pharmaceutically acceptable acid addition salts. The above compounds are useful as medicine in human and animal therapy, which act on the central nervous system, for example, as muscle relaxants, anticonvulsants, sedatives, minor tranquilizers, etc.

31 Claims, No Drawings

THIENODIAZEPINE DERIVATIVES

This invention relates to new thienodiazepine derivatives useful as medicines which are represented by the general formula (I),

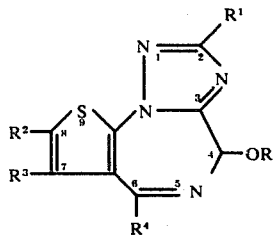

wherein $R^1$ represents a carboxyl group which may be esterified or amidated; each of $R^2$ and $R^3$ represents hydrogen atom or a lower alkyl group, or $R^2$ and $R^3$ may bond to each other to form an alkylene group; $R^4$ represents a phenyl group which may have substituent; and R represents hydrogen atom, and acyl group or an alkyl group, and to processes for producing the same.

The following classes of compounds (I-a), (I-b) and (I-c) are included within the scope of the compound (I) of the present invention.

a. Compound (I) wherein R is an acyl group:

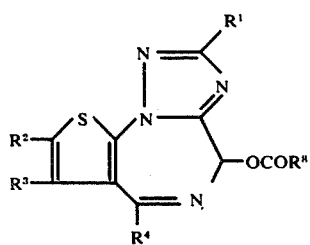

wherein $R^8$ represents an alkyl, aryl or aralkyl group, and other symbols are as defined above;

b. compound (I) wherein R is hydrogen atom:

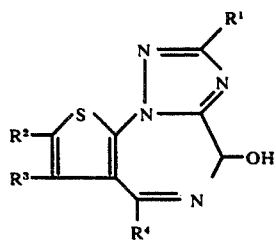

wherein all symbols are as defined above; and c. compound (I) wherein R is an alkyl group:

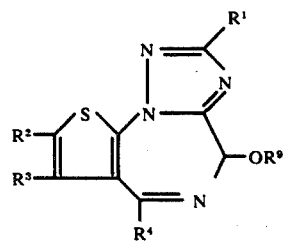

wherein $R^9$ represents an alkyl group and other symbols are as defined above.

In the above-mentioned general formulae, when the carboxyl group represented by $R^1$ is esterified, it is represented by the general formula, $-COOR^5$, wherein $R^5$ represents a lower alkyl group having 1 to 4 carbon atoms, such as methyl, ethyl, propyl, isopropyl, butyl, isobutyl, sec-butyl and tert-butyl groups. When the carboxyl group represented by $R^1$ is amidated, the said carboxyl group is represented by the general formula

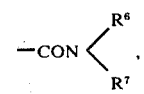

wherein each of $R^6$ and $R^7$ represents hydrogen atom, or an alkyl group which may have a lower alkoxy group as a substituent, or $R^6$ and $R^7$ may form a heterocyclic ring together with the nitrogen atom adjacent thereto. The alkyl groups represented by $R^6$ and $R^7$ include, in addition to the same lower alkyl groups having 1 to 4 carbon atoms as represented by $R^5$, alkyl groups having 1 to 6 carbon atoms, which may be straight, branched or cyclic, such as cyclopropylmethyl, pentyl, cyclopentyl, hexyl and cyclohexyl groups. Among them, lower alkyl groups having 1 to 3 carbon atoms are preferred. When the alkyl groups represented by $R^6$ and $R^7$ have a lower alkoxy group as a substituent, the said alkoxy groups are preferably lower alkoxy groups having 1 to 4 carbon atoms, such as methoxy, ethoxy, propoxy, isopropoxy and butoxy groups, for example. These alkoxy groups may be optional in number at optional positions of the alkyl groups represented by $R^6$ and $R^7$. Examples of the substituted alkyl groups represented by $R^6$ and $R^7$ include 2-methoxyethyl, 2-ethoxyethyl, 2,2-dimethoxyethyl, 2,2-diethoxyethyl, 3-methoxypropyl, 3-ethoxypropyl, 2-methoxypropyl and 2-ethoxypropyl groups. When $R^6$ and $R^7$ form a heterocyclic ring together with the nitrogen atom adjacent thereto, such heterocyclic ring is preferably a 5- to 6-membered ring, which may contain another 1 or 2 nitrogen and/or oxygen atoms as hetero atoms. Examples of such heterocyclic ring include pyrrolidine, piperidine, morpholine, N-mono-substituted piperazine (e.g. N-methyl-, N-ethyl-, N-propyl and N-(2-methoxyethyl)-piperazine), etc. Among the substituents represented by $R^1$, the amidated carboxyl group, especially carboxamide group (i.e. $R^6$ and $R^7$ of

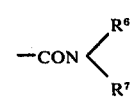

are both hydrogen), is preferred.

Preferred lower alkyl groups represented by $R^2$ and $R^3$ are straight or branched lower alkyl groups having 1 to 4 carbon atoms such as methyl, ethyl, propyl, isopropyl, butyl, isobutyl, sec-butyl, tert-butyl etc. When $R^2$ and $R^3$ form an alkylene group, the alkylene group is preferably a trimethylene or tetramethylene group, for example. As the substituents represented by $R^2$ and $R^3$, hydrogen atom and a lower alkyl group are preferred.

The phenyl group represented by $R^4$ is unsubstituted or substituted. When the phenyl group represented by $R^4$ has a substituent, the substituent may be optional in number at any substitutable position on the phenyl nucleus. Most preferable number of the substituent is one. Halogen atom, lower alkyl, lower alkoxy and polyhalo-lower alkyl groups are preferable as such substituents. Examples of the halogen atom are chlorine, bromine, iodine and fluorine; examples of the lower alkyl group are the same lower alkyl groups having about 1 to 4 carbon atoms as represented by $R^2$ and $R^3$; and examples of the lower alkoxy group are the same lower alkoxy groups having about 1 to 4 carbon atoms as those of the substituent of the alkyl groups represented by $R^6$ and $R^7$. Examples of the polyhalo-lower alkyl group are trifluoromethyl and trichloromethyl group. Among the substituents of the phenyl group, halogen atom is preferred, and as the position of the substituent, ortho-position of the phenyl ring is particularly preferred. The acyl group represented by R is represented by the formula —$COR^8$, wherein $R^8$ represents an alkyl, aryl or aralkyl group. Examples of the alkyl group represented by $R^8$ are the same lower alkyl groups having about 1 to 4 carbon atoms as represented by $R^9$, $R^2$ or $R^3$; examples of the aryl group represented by $R^8$ are phenyl and tolyl groups; and examples of the aralkyl group represented by $R^8$ are benzyl and phenethyl groups. Among the acyl groups represented by R, those of the general formula —$COR^8$ wherein $R^8$ is the lower alkyl (i.e. lower alkyl carbonyl) are preferred.

When R represents alkyl group designated by $R^9$, $R^9$ represents same lower alkyl group having 1 to 4 carbon atoms as those represented by $R^2$ and $R^3$.

In the formulae described hereinafter, all symbols have the same meanings as defined above;

The class of the compounds (I-a) of the present invention can be produced by the following processes:

a. a process which comprises (step A) reacting a compound (II):

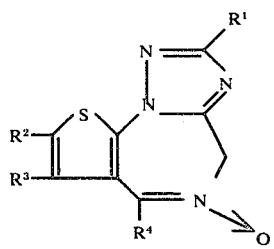

with a reactive derivative of a carboxylic acid of the general formula $R^8$ COOH; and b. a process which comprises (step E) reacting a compound (I-b);

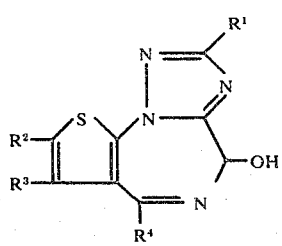

with an esterifying agent capable of converting the hydroxyl group at 4-position of the compound (I-b) into acyloxy group of the general formula —$OCOR^8$.

The class of the compounds (I-b) of the present invention can be produced by the following processes:

c. a process which comprises (step C) subjecting a compound (I-a):

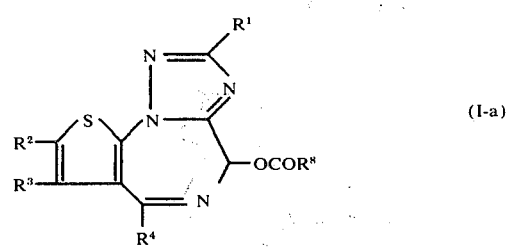

to hydrolysis; and d. a process which comprises (step A) reacting a compound (II);

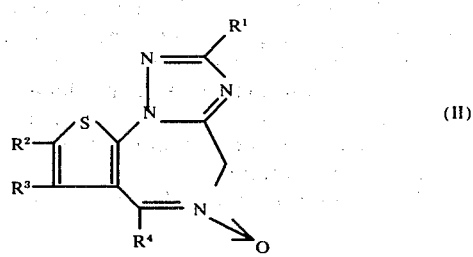

with a reactive derivative of a carboxylic acid of the general formula $R^8COOH$ to produce a compound (I-a):

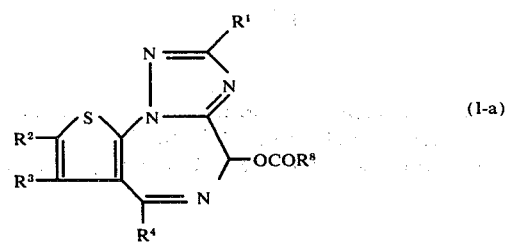

and then (step C) subjecting the thus obtained compound to hydrolysis.

The class of the compounds (I-c) of the present invention can be produced by the following processes:

e. a process which comprises (step B) reacting a compound (I-a):

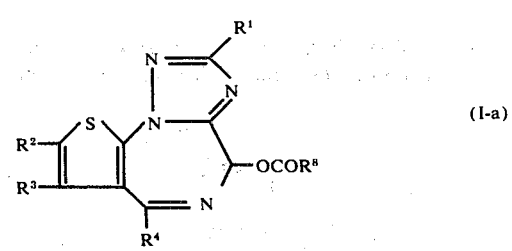

with a compound of the general formula $R^9OH$;

f. a process which comprises (step A) reacting a compound (II);

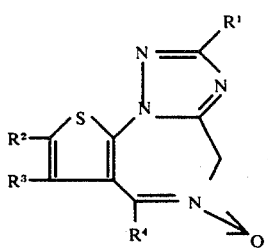
(II)

with a reactive derivative of a carboxylic acid of the general formula $R^8COOH$ to produce a compound (I-a):

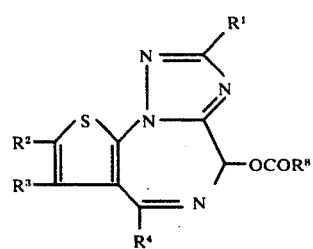
(I-a)

and then (step B) reacting the thus obtained compound with a compound of the general formula $R^9OH$;

g. a process which comprises (step D) reacting a compound (I-b):

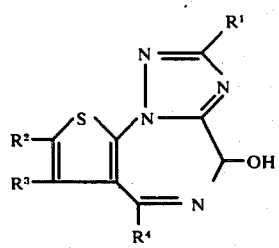
(I-b)

with a compound of the general formula $R^9OH$;

h. a process which comprises (step C) subjecting a compound (I-a):

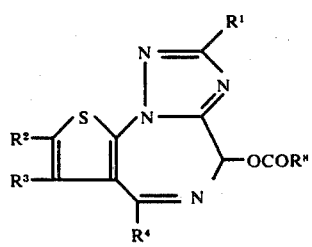
(I-a)

to hydrolysis to produce a compound (I-b):

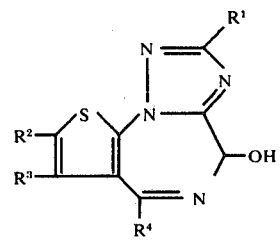
(I-b)

and then (step D) reacting the thus obtained compound with a compound of the general formula $R^9OH$; and i. a process which comprises (step A) reacting a compound (II):

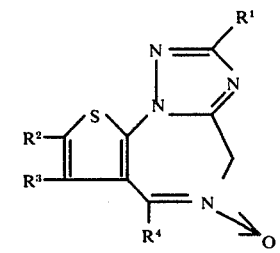
(II)

with a reactive derivative of a carboxylic acid of the general formula $R^8COOH$ to produce a compound (I-a):

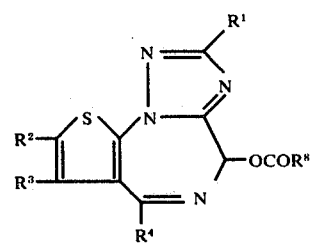
(I-a)

then (step C) subjecting the thus obtained compound to hydrolysis to produce a compound (I-b):

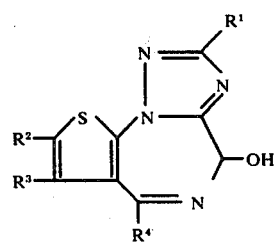
(I-b)

and further reacting the thus obtained compound with a compound of the general formula $R^9OH$.

The reactions involved in the processes of the present invention are summarized in the following reaction scheme:

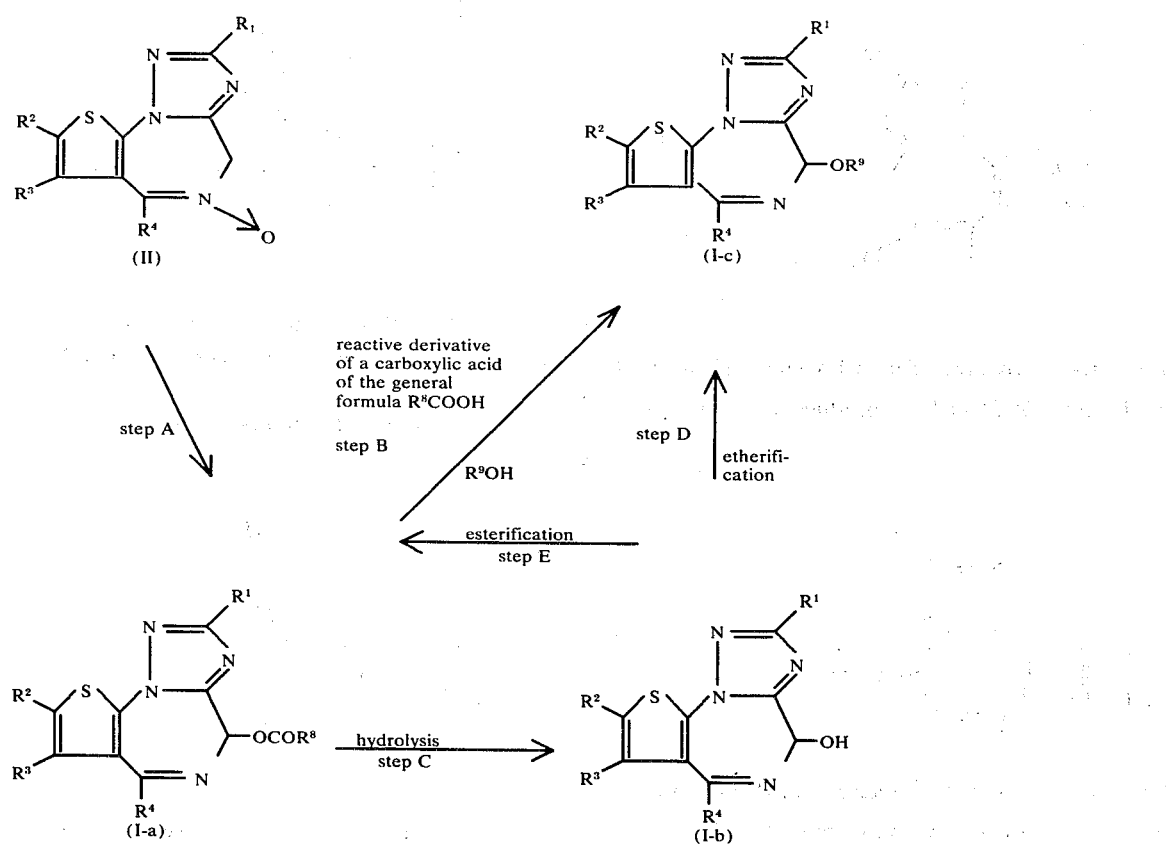

In the above reaction scheme, all symbols have the same meanings as defined above.

The reaction of the step (A) of the present invention is carried out by reacting a compound (II) with a reactive derivative of a carboxylic acid of the general formula $R^8COOH$. Examples of the reactive derivative of the carboxylic acid to be used in the reaction are acid halides of carboxylic acids represented by the general formula $R^8COOH$, wherein $R^8$ is as defined above (e.g. acid chlorides, acid bromides, etc.), acid anhydrides thereof, and sulfides represented by the formula $(R^8CO)_2S$. The amount of the reactive derivative of the carboxylic acid to be used is usually about 2 to 5 moles per mole of the compound (II). The reaction is ordinarily carried out in the presence of a solvent with or without heating at a temperature in the range from about 0° to about 200° C. As the solvent, there may be used, for example, any of dimethylformamide, tertiary organic amines (e.g. pyridine, picoline), and carboxylic acids represented by the aforesaid formula $R^8COOH$. When the reactive derivative of the carboxylic acid to be used in the reaction is liquid, the reactive derivative may be used in excess so as to serve also as the solvent. By the reaction of this step, there is prepared the compound (I-a) in which an acyloxy group corresponding to the reactive derivative used is introduced in the 4-position of the starting compound (II).

The reaction of the step (B) of the present invention is an alcoholysis of the compound (I-a). The alcoholysis of the compound (I-a) is conducted by reacting the compound (I-a) with an alcohol of the formula $R^9OH$, wherein $R^9$ is as defined above. The amount of the alcohol to be used is at least equimolar relative to the compound (I-a), and is not particularly limited. Usually, the reaction is conducted preferably in the presence of an acid, and does not necessarily require the use of solvent since the alcohol used also serves as a solvent, but a halogenated hydrocarbon (e.g. chloroform or dichloromethane) may be used as the solvent. The reaction temperature is ordinarily from room temperature to about the boiling point of the alcohol and/or solvent used. Examples of the acid to be used in the reaction include mineral acids (e.g. hydrochloric, sulfuric and phosphoric acids), carboxylic acids (e.g. acetic acid and propionic acid), and organic sulfonic acids (e.g. toluenesulfonic acid and methanesulfonic acid).

The reaction of the step C is a hydrolysis of the compound (I-a). The hydrolysis may be any one known per se which can convert the acyloxy group at 4-position of the compound (I-a) into hydroxy group. For example the hydrolysis is usually conducted by treating the compound (I-a) with a basic substance around room temperature in the presence or absence of a solvent. Examples of the solvent are lower alkanols (e.g. methanol, ethanol, propanol, etc.), dioxane and tetrahydrofuran. In some cases, the reaction may be carried out under suitable heating (e.g. at around the boiling point of the solvent used). Examples of the basic substance are alkali metal hydroxides or carbonates (e.g. sodium hydroxide, potassium hydroxide, sodium carbonate, potassium carbonate), ammonia, etc.

The reaction of the step D is an etherification of the compound (I-b). The etherification is conducted by reacting the compound (I-b) with an alcohol corresponding to $-OR^9$, preferably in the presence of an acid. As the alcohols and the acids, those used in the alcoholysis of the step B may also be used. The reactant alcohol may take a role as a solvent of the reaction and therefore any other solvent is not especially required. However, there may be used the same solvents as used in the alcoholysis of the step B under the same reaction conditions as in said alcoholysis.

The reaction of step E is an esterification of the compound (I-b). The esterification is conducted by reacting the compound (I-b) with an esterifying agent capable of converting the hydroxy group at 4-position of the compound (I-b) into an acyloxy group. As the esterifying agents, there may be used any of the reactive derivatives of carboxylic acid employed in the step (A), usually in amounts of about 1 to 3 moles per mole of the starting compound. The reaction is generally carried out in the presence of a solvent at room temperature to around the boiling point of the solvent used. As the solvent, there may be usually used chloroform, pyridine or dimethylformamide. However, when the reactive derivative of carboxylic acid used is liquid, the reactive derivative may be used in excess so as to serve also as the solvent.

Since the object compounds (I) of the present invention have basic nitrogen atoms in nucleus thereof, they can be converted into corresponding acid addition salts by treatment with inorganic acids (e.g. hydrochloric, hydrobromic, sulfuric, nitric and phosphoric acids) or organic acids (e.g. oxalic, succinic, malonic, tartaric, fumaric, maleic, methanesulfonic and p-toluenesulfonic acids) by conventional means (e.g. by treating compound (I) with said acids in the presence or absence of solvent, and, if necessary, by heating).

The thus produced object compounds (I) or their acid addition salts have pharmacological effects acting on the central nervous system, such as muscle relaxant, anticonvulsant, sedative, antianxiety, tranquilizing and sleep inducing effects, and hence are useful as medicines in human and animal therapy such as muscle relaxants, anticonvulsants, sedatives, antianxiety agents, minor tranquilizers, hypnotics, etc. The compounds (I) and their pharmaceutically acceptable acid addition salts are orally or parenterally administrable as such or in a suitable form such as powder, granules, tablets, capsules, or injectable solutions admixed with pharmaceutically acceptable carriers, excipients or diluents. The dose of the compounds (I) or their salts to be administered varies with the kind and severity of the diseases to be treated, the clinical conditions and the kind of the compound, but is usually in the range from about 0.1 to 100 mg. for oral administration for an adult human per day.

The starting compounds (II) used in the present invention can be produced according to the procedure shown by the following reaction scheme:

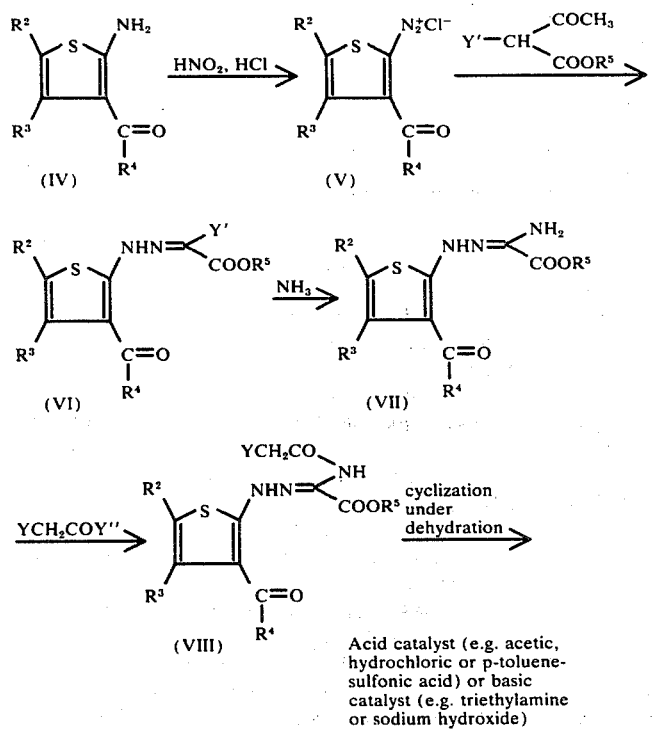

-continued

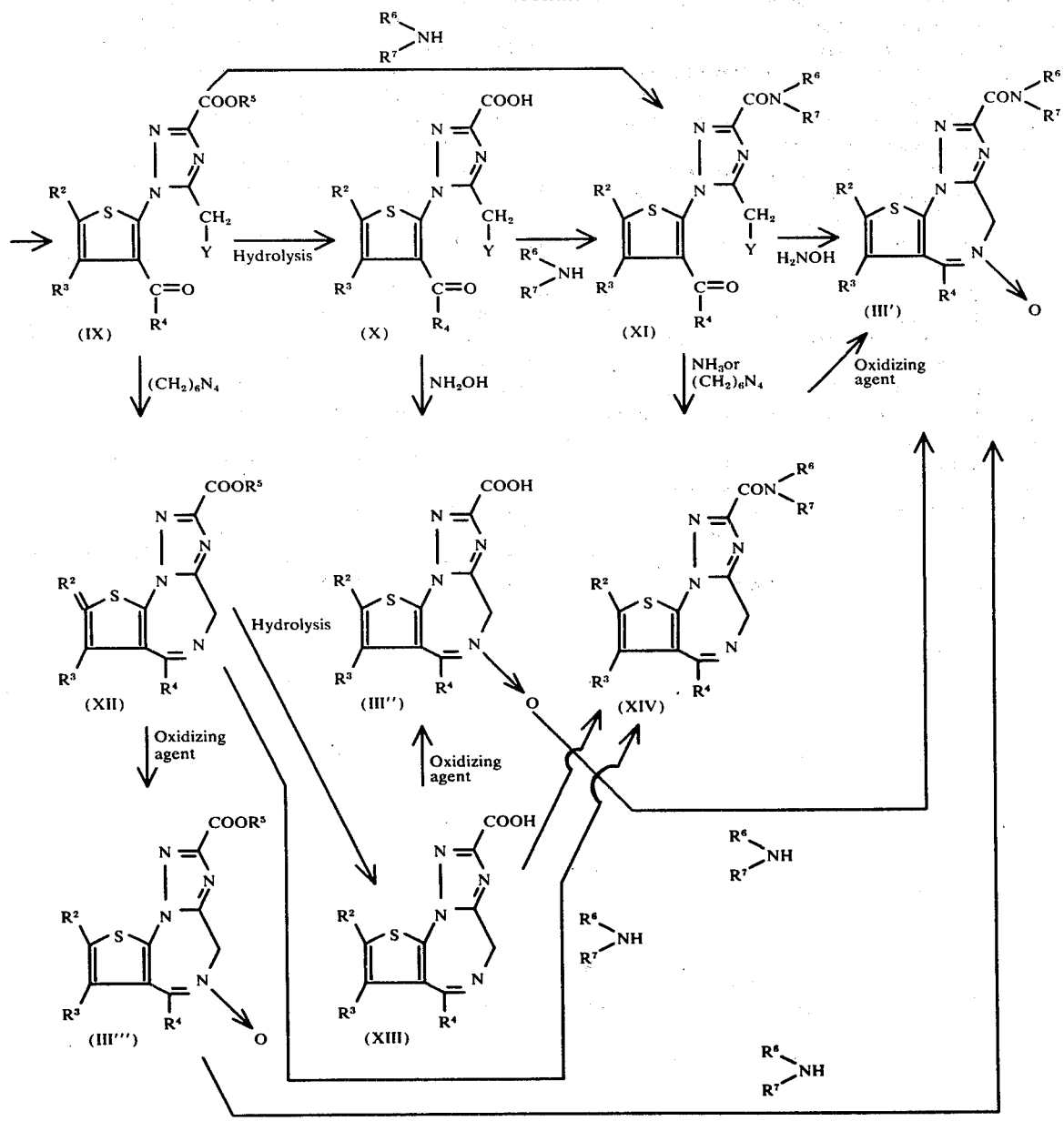

wherein each of Y, Y' and Y'' represents a halogen atom (e.g. chlorine, bromine and iodine); $R^1$ to $R^7$ are as defined above; and the oxidizing agent is hydrogen peroxide or an organic peracid (e.g. perbenzoic or m-chloroperbenzoic acid.

Specific compounds as represented by the general formula (I), inclusive of those as shown in Examples which are set forth for illustrative but not limiting purpose, are as follows;

1. 4-Acetoxy-6-phenyl-4H-thieno[3,2-f]-s-triazolo[1,5-a][1,4-diazepine-2-carboxamide
2. 4-Methoxy-6-phenyl-4H-thieno[3,2-f]-s-triazolo[1,5-a]-[1,4]diazepine-2-carboxamide
3. 4-Acetoxy-7,8-diemthyl-6-phenyl-4H-thieno[3,2-f]-s-triazolo[1,5-a][1,4]diazepine-2-carboxamide
4. 4-Hydroxy-7,8-dimethyl-6-phenyl-4H-thieno[3,2-f]-s-triazolo[1,5-a][1,4]diazepine-2-carboxamide
5. 4-Methoxyl-7,8-diemthyl-6-phenyl-4H-thieno[3,2-f]-s-triazolo[1,5-a][1,4]diazepine-2-carboxamide
6. 4-Acetoxy-N,N,7,8-tetramethyl-6-phenyl-4H-thieno[3,2-f]-s-triazolo[1,5-a][1,4]diazepine-2-carboxamide
7. 4-Methoxy-N,N,7,8-tetramethyl-6-phenyl-4H-thieno[3,2-f]-s-triazolo[1,5-a][1,4]diazepine-2-carboxamide
8. 4-Acetoxy-7,8-dimethyl-6-phenyl-2-piperidinocarbonyl-4H-thieno[3,2-f]-s-triazolo[1,5-a][1,4]diazepine
9. 4-Hydroxy-7,8-dimethyl-6-phenyl-2-piperidinocarbonyl-4H-thieno[3,2-f]-s-triazolo[1,5-a][1,4]diazepine
10. 4-Methoxy-7,8-dimethyl-6-phenyl-2-piperidinocarbonyl-4H-thieno[3,2-f]-s-triazolo[1,5-a][1,4]diazepine
11. 4-Acetoxy-8-ethyl-6-phenyl-4H-thieno[3,2-f]-s-triazolo-[1,5-a][1,4]diazepine-2-carboxamide
12. 8-Ethyl-4-hydroxy-6-phenyl-4H-thieno[3,2-f]-s-triazolo-[1,5-a][1,4]diazepine-2-carboxamide
13. 8-Ethyl-4-methoxy-6-phenyl-4H-thieno[3,2-f]-s-triazolo-[1,5-a][1,4]diacepine-2-carboxamide 14. Ethyl 4-acetoxy-6-(2-chlorophenyl)-8-ethyl-4H-thieno-[3,2-f]-s-triazolo[1,5-a][1,4]diazepine-2-carboxylate 15. Ethyl 6-(2-chlorophenyl)-4-ethoxy-8-ethyl-4H-thieno-[3,2-f]-s-triazolo[1,5-a][1,4]diazepine-2-carboxylate 16. 4-Acetoxy-6-(2-chlorophenyl)-8-ethyl-4H-thieno[3,2-f]s-triazolo[1,5-a][1,4]diazepine-2-carboxamide 17. 4-Benzoyloxy-6-(2-chlorophenyl)-8-ethyl-4H-thieno-[3,2-f]-s-triazolo[1,5-a][1,4]diazepine-2-carboxamide 18. 6-(2-Chlorophenyl)-8-ethyl-4-phenylacetyloxy-4H-thieno-[3,2-f]-s-triazolo[1,5-a][1,4]diazepine-2-carboxamide 19. 6-(2-Chlorophenyl)-8-ethyl-4-hydroxy-4H-thieno-[3,2-f]s-triazolo[1,5-a][1,4]diazepine-2-carboxamide 20. 6-(2-Chlorophenyl)-8-ethyl-4-methoxy-4H-thieno[3,2-f]s-triazolo[1,5-a][1,4]diazepine-2-carboxamide 21. 6-(2-Chlorophenyl)-4-ethoxy-8-ethyl-4H-thieno[3,2-f]-s-triazolo[1,5-a][1,4]diazepine-2-carboxamide 22. 4-Acetoxy-6-(2-chlorophenyl)-8-ethyl-N-methyl-4H-thieno-[3,2-f]-s-triazolo[1,5-a][1,4]diazepine-2-carboxamide 23. 6-(2-Chlorophenyl)-8-ethyl-4-hydroxy-N-methyl-4H-thieno-[3,2-f]-s-triazolo[1,5-a][1,4]diazepine-2-carboxamide 24. 6-(2-Chlorophenyl)-8-ethyl-4-methoxy-N-methyl-4H-thieno-[3,2-f]-s-triazolo[1,5-a][1,4]diazepine-2-carboxamide 25. 4-Acetoxy-6-(2-chlorophenyl)-8-ethyl-N,N-dimethyl-4H-thieno[3,2-f]-s-triazolo-[1,5-a][1,4]diazepine-2-carboxamide 26. 6-(2-Chlorophenyl)-8-ethyl-4-hydroxy-N,N-dimethyl-4H-thieno[3,2-f]-s-triazolo[1,5-a][1,4]diazepine-2-carboxamide 27. 6-(2-Chlorophenyl)-8-ethyl-4-methoxy-N,N-dimethyl-4H-thieno[3,2-f]-s-triazolo[1,5-a][1,4]diazepine-2-carboxamide 28. 4-Acetoxy-6-(2-chlorophenyl)-8-ethyl-N-(2-methoxyethyl)-4H-thieno[3,2-f]-s-triazolo[1,5-a][1,4]diazepine-2-carboxamide 29. 6-(2-Chlorophenyl)-8-ethyl-4-methoxy-N-(2-methoxyethyl)-4H-thieno[3,2-f]-s-triazolo[1,5-a][1,4]diazepine-2-carboxamide 30. 4-Acetoxy-6-(2-chlorophenyl)-8-ethyl-2-pyrrolidinocarbonyl-4H-thieno-[3,2-f]-s-triazolo[1,5-a][1,4]diazepine 31. 6-(2-Chlorophenyl)-8-ethyl-4-methoxy-2-pyrrolidinocarbonyl-4H-thieno[3,2-f]-s-triazolo[1,5-a][1,4]diazepine 32. 4-Acetoxy-6-(2-chlorophenyl)-8-ethyl-2-piperidinocarbonyl-4H-thieno[3,2-f]-s-triazolo[1,5-a][1,4]diazepine 33. 6-(2-Chlorophenyl)-8-ethyl-4-hydroxy-2-piperidinocarbonyl-4H-thieno[3,2-f]-s-triazolo[1,5-a][1,4]diazepine 34. 4-Acetoxy-6-(2-chlorophenyl)-8-ethyl-2-morpholinocarbonyl-4H-tieno[3,2-f]-s-triazolo[1,5-a][1,4]diazepine 35. 6-(2-Chlorophenyl)-8-ethyl-4-methoxy-2-morpholinocarbonyl-4H-thieno[3,2-f]-s-triazolo[1,5-a][1,4]diazepine 36. 4-Acetoxy-6-(2-chlorophenyl)-8-ethyl-2-(4-methylpiperazino)-carbonyl-4H-thieno[2,2-f]-s-triazolo[1,5-a][1,4]diazepine 37. 6-(2(Chlorophenyl)-8-ethyl-4-methoxy-2-(4-methylpiperazino)-carbonyl-4H-thieno[3,2-f]-s-triazolo(1,5-a][1,4]diazepine 38. 4-Acetoxy-8-ethyl-6-(2-fluorophenyl)-4H-thieno[3,2-f]-s-triazolo[1,5-a][1,4]diazepine-2-carboxamide 39. 8-(Ethyl-6-(2-fluorophenyl)-4-hydroxy-4H-thieno[3,2-f]-s-triazolo[1,5-a][1,4]diazepine-2-carboxamide 40. 8-Ethyl-6-(2-fluorophenyl)-4-methoxy-4H-thieno[3,2-f]-s-triazolo[1,5-a][1,4]diazepine-2-carboxamide 41. 4-Acetoxy-8-ethyl-6-(2,6-difluorophenyl)-4H-thieno-[3,2-f]-s-triazolo[1,5-a][1,4]diazepine-2-carboxamide 42. 8-Ethyl-6-(2,6-difluorophenyl)-4-methoxy-4H-thieno[3,2-f]-s-triazolo[1,5-a][1,4]diazepine-2-carboxamide 43. 4-Acetoxy-6-(2-chlorophenyl)-8-methyl-4H-thieno[3,2-f]-s-triazolo[1,5-a][1,4]diazepine-2-carboxamide 44. 6-(2-Chlorophenyl)-4-methoxy-8-methyl-4H-thieno[3,2-f]-s-triazolo[1,5-a][1,4]diazepine-2-carboxamide 45. 4-Acetoxy-6-(2-chlorophenyl)-8-n-propyl-4H-thieno[3,2-f]-s-triazolo[1,5-a][1,4]diazepine-2-carboxamide 46. 6-(2-Chlorophenyl)-4-methoxy-8-n-propyl-4H-thieno[3,2-f]-s-triazolo[1,5-a][1,4]diazepine-2-carboxamide

PREPARATIVE EXAMPLE 1 a. To a stirred solution of 26.6 g. of 2-amino-3-(2-chlorobenzoyl)-5-ethylthiophene in 200 ml. of acetic acid and 30 ml. of concentrated hydrochloric acid is added dropwise a solution of 7.0 g. of sodium nitrite in 30 ml. of water under cooling on an ice-sodium chloride bath to prepare the corresponding diazonium salt solution. Then, the diazonium salt solution is added dropwise under cooling and stirring into a solution of 18.0 g. of ethyl 2-chloroacetoacetate and 40 g. of potassium acetate in 400 ml. of water. After the addition, the resulting solution is further stirred at room temperature for 1 hour, diluted with water and extracted with ether. After the ether layer is washed with water and dried over sodium sulfate, the solvent is removed by distillation The residue is dissolved in a mixture of ether and n-hexane and passed through a column containing 1 kg. of silica gel. Then, the fractions eluted with a mixture of ether and n-hexane (1:4) is combined and evaporated. The residue is crystallized from n-hexane to give ethyl [3-(2-chlorobenzoyl)-5-ethyl-2-thienyl]azochloroacetate as crystals. Recrystallization from ethanol gives yellow needles melting at 55° to 57° C.

Elemental analysis: $C_{17}H_{16}Cl_2N_2O_3S$; Calculated: C,51.13, H4.04, N,7.02; Found: C,51.05, H3.82, N,6.98.

b. 2Amino-3-benzoyl-4,5-dimethylthiophene is diazotized in the same manner as in a), and the produced diazonium salt is subjected to coupling with 2-chloroacetoacetic acid. The product is then purified by silica-gel column chromatography to give ethyl (3-benzoyl-4,5-dimethyl-2-thienyl)azo-chloroacetate as crystals. Recrystallization from isopropyl ether gives yellow needles melting at 96° to 97° C.

PREPARATIVE EXAMPLE 2 a. 16.0 g. of ethyl [3-(2-chlorobenzoyl)-5-ethyl-2-thienyl]azochloroacetate are added under ice-cooling to 160 ml. of saturated ethanolic ammonia. After 15 minutes, ice-water is added to the resulting solution, which is then extracted with ethyl acetate. The ethyl acetate layer is washed with water and dried over sodium sulfate, followed by evaporation of the solvent to give ethyl [3-(2-chlorobenzoyl)-5-ethyl-2-thienyl-]azoaminoacetate as an oily product. Then, the oily product is dissolved in 160 ml. of benzene. After addition of 11 g. of anhydrous potassium carbonate, 6.0 ml. of chloroacetylchloride are added dropwise with stirring into the mixture. The reaction is further conducted for 2 hours. After the resultant is cooled with ice, water and ethyl acetate are added thereto. The resulting solution is well shaken and the organic layer is separated. The organic layer is washed with water and dried over sodium sulfate. Then, the solvent is evaporated to give ethyl [3-(2-chlorobenzoyl)-5-ethyl-2-thienyl]azochloroacetylaminoacetate as crystals. Recrystallization from ethanol yields yellow needles melting at 136° to 137° C.

Elemental analysis: $C_{19}H_{19}Cl_2N_3O_4S$; Calculated: C,50.00, H,4.20, N,9.21; Found: C,49.98, H,4.08, N,9.28.

b. Ethyl (3-benzoyl-4,5-dimethyl-2-thienyl)azochloroacetate is treated with saturated ammoniacal ethanol in the same manner as in a), and the product is reacted with chloroacetyl chloride to give ethyl (3-benzoyl-4,5-dimethyl-2-thienyl)azo-chloroacetylaminoacetate as crystals, melting at 123° to 125° C.

PREPARATIVE EXAMPLE 3 a. A mixture of 4.44 g. of ethyl [3-(2-chlorobenzoyl)-5-ethyl-2-thienyl]azochloroacetylaminoacetate, 1.90 g. of p-toluenesulfonic acid (monohydrate) and 80 ml. of benzene is refluxed for 40 minutes, then washed successively with an aqueous solution of sodium hydrogen carbonate and water, and dried over sodium sulfate. Thereafter, the solvent is evaporated to give ethyl 1-[3-(2-chlorobenzoyl)-5-ethyl-2-thienyl]-5-chloromethyl-1H-1,2,4-triazole-3-carboxylate as crystals. Recrystallization from ethanol yields pale yellow prisms melting at 114° to 115° C.

Elemental analysis: $C_{19}H_{17}Cl_2N_3O_3S$; Calculated: C,52.06, H,3.91, N,9.59; Found: C,52.09, H,3.92, N,9.76.

b. Treatment of ethyl (3-benzoyl-4,5-dimethyl-2-thienyl)azochloroacetylaminoacetate with p-toluenesulfonic acid (monohydrate) in the same manner as in a) gives ethyl 1-(3-benzoyl-4,5-dimethyl-2-thienyl)-5-chloromethyl-1H-1,2,4-triazole-3-carboxylate as crystals. Recrystallization from methanol gives colorless prisms melting at 117° to 118° C.

PREPARATIVE EXAMPLE 4 a. A mixture of 3.50 g. of ethyl 1-[3-(2-chlorobenzoyl)-5-ethyl-2-thienyl]-5-chloromethyl-1H-1,2,4-triazole-3-carboxylate, 3.36 g. of hexamethylenetetramine and 80 ml. of ethanol is refluxed for 15 hours, followed by concentration. Then, addition of water to the residue gives ethyl 6-(2-chlorophenyl)-8-ethyl-4H-thieno[3,2-f]-s-triazolo[1,5-a][1,4]-diazepine-2-carboxylate as crystals. Recrystallization from ethanol yields pale yellow prisms melting at 147.5° to 148.5° C.

b. A mixture of ethyl 1-(3-benzoyl-4,5-dimethyl-2-thienyl)-5-chloromethyl-1H-1,2,4-triazole-3-carboxylate, hexamethylenetetramine and ethanol is refluxed for 4 hours in the same manner as in a) to give ethyl 7,8-dimethyl-6-phenyl-4H-thieno[3,2-f]-s-triazolo[1,5-a][1,4]diazepine-2-carboxylate as colorless plates melting at 173° to 174° C.

PREPARATIVE EXAMPLE 5 a. To a solution of 0.3 g. of ethyl 1-(3-benzoyl-4,5-dimethyl-2-thienyl)-5-chloromethyl-1H-1,2,4-triazole-3-carboxylate in 5 ml. of methanol is added 1 ml. of 2N-sodium hydroxide. After the mixture is stirred for 1 hour at room temperature, the resulting solution is neutralized with 2N-hydrochloric acid, then diluted with water and extracted with chloroform. After the chloroform layer is washed with water and dried over sodium sulfate, the solvent is evaporated. Recrystallization of the residue from methanol yields 1-(3-benzoyl-4,5-dimethyl-2-thienyl)-5-chloromethyl-1H-1,2,4-triazole-3-carboxylic acid as crystals melting at 162° to 163° C.

Elemental analysis: $C_{17}H_{14}ClN_3O_3S$; Calculated: C,54.33, H,3.76; N,11.18; Found: C,54.59; H,3.45, N,11.19.

b. Hydrolysis of 0.438 g. of ethyl 1-[3-(2-chlorobenzoyl)-5-ethyl-2-thienyl]-5-chloromethyl-1H-1,2,4-triazole-3-carboxylate is hydrolyzed with sodium hydroxide in the same manner as in a) gives 1-[3-(2-chlorobenzoyl)-5-ethyl-2-thienyl]-5-chloromethyl-1H-1,2,4-triazole-3-carboxylic acid as an oily substance. Infra red absorption spectrum (neat): $1735 cm^{-1}$(-COOH), $1665 cm^{-1}$(C=O).

PREPARATIVE EXAMPLE 6

A solution of 0.3 g. of ethyl 6-(2-chlorophenyl)-8-ethyl-4H-thieno[3,2-f]-s-triazolo[1,5-a][1,4]diazepine-2-carboxylate in 4 ml. of dichloromethane is cooled to 0° to 5° C. To this solution is added a solution of 0.4 g. of 70% n-chloroperbenzoic acid in 6 ml. of dichloromethane, and the resulting mixture is allowed to stand in a refrigerator for 3.5 days. Then, the reaction solution is washed successively with an aqueous solution of sodium hydrogen carbonate an aqueous sodium thiosulfate solution, an aqueous sodium hydrogen carbonate solution and water, and dried over sodium sulfate. After evaporation of the solvent addition of ethanol to the residue gives 6-(2-chlorophenyl)-2-ethoxycarbonyl-8-ethyl-4H-thieno[3,2-f]-s-triazolo[1,5-a][1,4]-diazepine-5-oxide as crystals. Recrystallization from dichloromethane-ethanol gives colorless prisms melting at 193° to 194° C.

Elemental analysis: $C_{19}H_{17}ClN_4O_3S$; Calculated: C,54.74, H,4.11, N,13.44, Found: C,54.49, H,4.02, N,13.60.

PREPARATIVE EXAMPLE 7 a. A mixture of 4.38 g. of ethyl 1-[3-(2-chlorobenzoyl)-5-ethyl-2-thienyl]-5-chloromethyl-1H-1,2,4-triazole-3-carboxylate and 50 ml. of saturated ethanolic ammonia is heated in a sealed tube for 1.5 hours on a water bath at 90° C. After cooling, the tube is opened, and the solvent is removed by distillation, and water is added to the residue to give 6-(2-chlorophenyl)-8-ethyl-4H-thieno[3,2-f]-s-triazolo-[1,5-a][1,4]diazepin-2-carboxamide as crystals. Recrystallization from methanol gives pale yellow prisms melting a 232° to 233° C.

Elemental analysis: $C_{17}H_{14}ClN_5OS$; Calculated: C,54.91, H,3.80, N,18.84; Found: C,54.58, H,3.49, N,19.00.

b. Treatment of a mixture of ethyl 1-(3-benzoyl-4,5-dimethyl-2-thienyl)-5-chloromethyl-1H-1,2,4-triazole-3-carboxylate and 20% ethanolic ammonia in a sealed tube in the same manner as in a) gives 7,8-dimethyl-6-phenyl-4H-thieno[3,2-f]-s-triazolo[1,5-a][1,4]diazepine-2-carboxamide as crystals. Recrystallization from ethyl acetate gives colorless prisms melting at 251° to 252° C.

PREPARATIVE EXAMPLE 8 a. To a mixture of 2.00 g. of ethyl 6-(2-chlorophenyl)-8-ethyl-4H-thieno[2,3-f]-s-triazolo[1,5-a][1,4]diazepine-2-carboxylate, 20 ml. of ethanol and 10 ml. of water is added with stirring 5 ml. of a 2N-aqueous potassium hydroxide solution, and the resulting mixture is stirred at room temperature for 40 minutes. Then, the reaction solution is acidified with acetic acid and the diluted with water to give 6-(2-chlorophenyl)-8-ethyl-4H-thieno[3,2-f]-s-triazolo[1,5-a][1,4]-diazepine-2-carboxylic acid as crystals. Recrystallization from hydrous ethanol gives colorless plates melting at 134° to 136° C. (softening). This product contains one mole of water of crystallization.

Elemental analysis: $C_{17}H_{13}ClN_4O_2S.H_2O$; Calculated: C,52.24, H,3.87, N,14.34; Found: C,52.67, H,3.72, N,14.40.

b. Treatment of ethyl 7,8-dimethyl-6-phenyl-4H-thieno [3,2-f]-s-triazolo[1,5-a][1,4-diazepine-2-carboxylate with a 2N-aqueous sodium hydroxide solution in the same manner as in a) gives 7,8-dimethyl-6-phenyl-4H-thieno[3,2-f]-s-triazolo[1,6-a][1,4]diazepin-2-carboxylic acid. Recrystallization ½ mole of methanol of crystallization), melting at 209 to 211° C. (decomposition).

PREPARATIVE EXAMPLE 9

To a solution of 0.169 g. of 7,8-dimethyl-6-phenyl-4H-thieno[3,2-f][-s-triazolo[1,5-a][1,4]diazepine-2-carboxylic acid in 3 ml. of tetrahydrofuran is added 0.10 ml. of triethylamine. To the resulting mixture is added 0.07 ml. of ethyl chlorocarbonate under stirring and cooling on an ice-sodium chloride bath, and the mixture is stirred for 5 minutes. Subsequently, 0.07 ml. of piperidine is added to the mixture, followed by stirring for 30 minutes, and water is added to the resulting mixture. Then, the mixture is extracted with ethyl acetate. The ethyl acetate layer is washed with water, dried over sodium sulfate, followed by evaporation of the solvent to give 7,8-dimethyl-6-phenyl-2-piperidinocarbonyl-4H-thieno[3,2-f]-s-triazolo[1,5-a][1,4]-diazepine as crystals. Recrystallization from ethyl acetate gives colorless prisms melting at 178° to 179° C.

Elemental analysis: $C_{22}H_{23}N_5OS$; Calculated: C,65.17, H,5.72, N,17.28; Found: C,65.63, H,5.43, N,17.42.

PREPARATIVE EXAMPLE 10

A mixture of 0.376 g. of 1-(3-benzoyl-4,5-dimethyl-2-thienyl)-5-chloromethyl-1H-1,2,4-triazole-3-carboxylic acid, 1.4g. of hydroxylamine hydrochloride, 1.46 g. of potassium carbonate, 0.15 g. of sodium iodide, 5 ml. of water and 5 ml. of ethanol is stirred for 1 hour on a water bath at 80° to 90° C. After cooling, the mixture is acidified with 6N-hydrochloric acid, diluted with water and then extracted with dichloromethane. The dichloromethane layer is washed with water, dried over sodium sulfate, and the solvent is evaporated to give 7,8-dimethyl-6-phenyl-4H-thieno[3,2-f]-s-triazolo[1,5-a][1,4]diazepine-2-carboxylic acid 5-oxide as crystals. Recrystallization from acetone gives colorless prisms melting at 224° to 226° C. (decomposition).

Elemental analysis: $C_{17}H_{14}N_4O_3S$; Calculated: C,57.62, H,3.98, N,15.81; Found: C,57.69, H,3.91, N,15.85.

PREPARATIVE EXAMPLE 11

To a mixture of 178 mg. of 7,8-dimethyl-6-phenyl-4H-thieno[3,2-f]-s-triazolo[1,5-a][1,4]diazepine-2-carboxylic acid 5-oxide, 0.1 ml. of triethylamine and 5 ml. of tetrahydrofuran is added 0.07 ml. of ethyl chlorocarbonate under stirring and cooling on an ice-sodium chloride bath, and the mixture is stirred for 5 minutes. Then, to the mixture is added 0.07 ml. of piperidine, followed by stirring for 30 minutes, and water is added to the resulting mixture. Then, the mixture is extracted with ethyl acetate. The ethyl acetate layer is washed with water, dried over sodium sulfate and then the solvent is evaporated. Thereafter, addition of ether to the residue gives 7,8-dimethyl-6-phenyl-2-piperidinocarbonyl-4H-thieno[3,2-f]-s-triazolo[1,5-a][1,4]diazepine-5-oxide as crystals. Recrystallization from ethyl acetate gives colorless prisms melting at 213° to 214° C.

Elemental analysis: $C_{22}H_{23}N_5O_2S$; Calculated: C,62.59, H,5.50, N,16.62; Found: C,62.54, H,5.33, N,16.30.

PREPARATIVE EXAMPLE 12 a. To a solution of 0.135 g. of 7,8-dimethyl-6-phenyl-4H-thieno[3,2-f]-s-triazolo[1,5-a][1,4-diazepine-2-carboxamide in 5 ml. of dichloromethane is added a solution of 0.18 g. of 70% m-chloroperbenzoic acid in 5 ml. of dichloromethane, and the resulting solution is left to stand at 5° C. for 5 days. Thereafter, to the reaction solution is added on aqueous sodium sulfate solution and aqueous sodium hydrogen carbonate solution, followed by stirring. The precipitated crystals are collected by filtration and recrystallized from acetone to give 2-carbamoyl-7,8-dimethyl-6-phenyl-4H-thieno[3,2-f]-s-triazolo[1,5-a]-[1,4]diazepine-5-oxide as colorless prisms melting at 281° to 283° C. (decomposition).

Elemental analysis: $C_{17}H_{15}N_5O_2S$; Calculated: C,57.78, H,4.28, N,19.82; Found: C,57.93; H,4.24, N,19.66.

b. Each of 7,8-dimethyl-6-phenyl-2-piperdinocarbonyl-4H-thieno[3,2-f]-s-triazolo[1,5-a][1,4]diazepine and 6-(2-chlorophenyl)-8-ethyl-4H-thieno[3,2-f]-s-triazolo[1,5-a]-[1,4]diazepine-2-carboxamide is treated with 70% m-chloroperbenzoic acid in the same manner as in a) to give 7,8-dimethyl-6-phenyl-2-piperidinocarbonyl-4H-thieno[3,2-f]-s-triazolo-[1,5-a][1,4]diazepine-5-oxide, as colorless prisms melting at 213° to 214° C. and 2-carbamoyl-6-(2-chlorophenyl)-8-ethyl-4H-thieno[3,2-f]-s-triazolo[1,5-a][1,4]diazepine-5-oxide as colorless needles melting at 247° to 248° C, repectively.

EXAMPLE 1

A mixture of 1.2 g. of 6--(2-chlorophenyl)-8-ethyl-4H-thieno[3,2-f]-s-triazolo[1,5-a][1,4]diazepine-2-carboxamide-5-oxide and 20 ml. of acetic anhydride is heated at 90° to 95° C. for 50 minutes, and then the solvent is evaporated. The residue is washed with ether to give 4-acetoxy-6-(2-chlorophenyl)-8-ethyl-4H-thieno[3,2-f]-s-triazolo[1,5-a][1,4]diazepine-2-carboxamide as crystals. Recrystallization from ethyl acetate gives colorless prisms melting at 168° to 170° C.

Elemental analysis: $C_{19}H_{16}ClN_5O_3S$; Calculated: C,53.08, H,3.75, N,16.29; Found: C,53.00, H,3.49, N,16.13.

Treatment of 7,8-dimethyl-6-phenyl-2-(1-piperidinocarbonyl)-4H-thieno[3,2-f]-s-triazolo[1,5-a][1,4]diazepine 5-oxide with acetic anhydride in the same manner as in the above gives 4-acetoxy-7,8-dimethyl-6-phenyl-2-piperidinocarbonyl-4H-thieno[3,2-f]-s-triazolo[1,5-a][1,4-diazepine as crystals. Recrystallization from ether gives colorless prisms melting at 168° to 169° C.

Elemental analysis: $C_{24}H_{25}N_5O_3S$; Calculated: C,62.19, H,5.44, N15.11; Found: C,61.92, H,5.44, N,15.05.

EXAMPLE 2

To a solution of 0.86 g. of 4-acetoxy-6-(2-chlorophenyl)-8-ethyl-4H-thieno[3,2-f]-s-triazolo[1,5-a][1,4]-diazepine-2-carboxamide in 5 ml. of methanol is added dropwise 2 ml. of a 1N-aqueous sodium hydroxide solution with stirring and ice-cooling. After 5 minutes, to the resulting mixture is added 2 ml. of a 1N-aqueous hydrochloric acid solution and then water. The resulting precipitate is collected by filtration and then washed with water to give 6-(2-chlorophenyl)-8-ethyl-4-hydroxy-4H-thieno[3,2-f]-s-triazolo[1,5-a]-[1,4]diazepine-2-carboxamide as crystals. Recrystallization from ethanol gives colorless prisms melting at 228° to 231° C.

Elemental analysis: $C_{17}H_{14}ClN_5O_2S$; Calculated: C,52.64, H,3.64, N,18.06; Found: C,52.97, H,3.30, N,18.08.

EXAMPLE 3

To a solution of 0.086 g. of 4-acetoxy-6-(2-chlorophenyl)-8-ethyl-4H-thieno[3,2-f]-s-triazolo[1,5-a][1,4]diazepine-2-carboxamide in 3 ml. of methanol is added one drop of concentrated sulfuric acid and the resulting mixture is refluxed for 5 minutes. After evaporation of the solvent a saturated aqueous sodium hydrogen carbonate solution is added to the residue. The resulting precipitate is collected by filtration to give 6-(2-chlorophenyl)-8-ethyl-4-methoxy-4H-thieno[3,2-f]-s-triazolo[1,5-a][1,4]diazepine-2-carboxamide as crystals. Recrystallization from ethyl acetate gives powdery crystals melting at 200° to 201° C.

Elemental analysis: $C_{18}H_{16}ClN_5O_2S$; Calculated: C,53.79, H,4.01, N,17.43; Found: C,53.90, H,4.04, N,17.08.

Treatment of 4-acetoxy-7,8-dimethyl-6-phenyl-2-piperidinocarbonyl-4H-thieno[3,2-f]-s-triazolo[1,5-a][1,4]-diazepine with methanol and concentrated sulfuric acid in the same manner as in the above Example gives 7,8-dimethyl-4-methoxy-6-phenyl-2-piperidinocarbonyl-4H-thieno[3,2-f]-s-triazolo[1,5-a][1,4]diazepine as an oily substance.

Infra Red Absorption Spectrum (neat liquid):

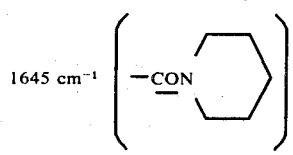

Mass Spectrum: M⁺ m/e: 435
Nuclear Magnetic Resonance Spectrum (CDCl₃), δ (ppm):
1.66 (3H, s., CH₃), 2.38 (3H, s., CH₃),
3.8 (3H, s., OCH₃), 5.36 (1H, broad s.,

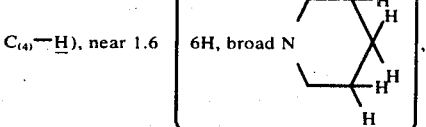

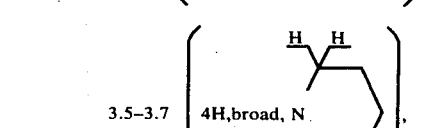

EXAMPLE 4

To a solution of 0.86 g. of 6-(2-chlorophenyl)-8-ethyl-4-hydroxy-4H-thieno[3,2-f]-s-triazolo[1,5-a][1,4]-diazepine-2-carboxamide in 20 ml. of methanol is added one drop of concentrated sulfuric acid. The resulting mixture is refluxed for 5 minutes. After evaporation of the solvent a saturated sodium hydrogen carbonate solution is added to the residue, and the resulting precipitate is collected by filtration to give 6-(2-chlorophenyl)-8-ethyl-4-methoxy-4H-thieno[3,2-f]-s-triazolo[1,5-a][1,4]diazepine-2-carboxamide as crystals melting at 200° to 201° C. This product is identical with the product obtained in Example 3 with respect to the melting point and infra red absorption spectrum thereof.

EXAMPLE 5

A mixture of 0.387 g. of 6-(2-chlorophenyl)-8-ethyl-4-hydroxy-4H-thieno[3,2-f]-s-triazolo[1,5-a][1,4-diazepine-2-carboxamide and 5 ml. of acetic anhydride is heated at 90° C. for 5 minutes, and then acetic anhydride is evaporated under reduced pressure. Then, the residue is washed with ethyl ether to give 4-acetoxy-6-(2-chlorophenyl)-8-ethyl-4H-thieno[3,2-f]-s-triazolo[1,5-a][1,4]-diazepine-2-carboxamide as crystals melting at 168° to 170° C. This product is identical with the product obtained in Example 1 with respect to the melting point and infra red absorption spectrum thereof.

EXAMPLE 6

An example of a composition in which a compound of this invention is utilized as a tranquilizer is as follows:

Tablet

| | | |
|---|---|---|
| (1) | 6-(2-chlorophenyl)-8-ethyl-4-hydroxy-4H-thieno[3,2-f]-s-triazolo-[1,5-a][1,4]diazepine-2-carboxamide | 1 mg |

Tablet-continued

| | | |
|---|---|---|
| (2) | lactose | 73 mg |
| (3) | corn starch | 40 mg |
| (4) | hydroxypropyl cellulose | 5.5 mg |
| (5) | magnesium stearate | 0.5 mg |
| | | 120.0 mg per tablet |

(1), (2), 9/10 Quantity of (3), and (4) are thoroughly mixed and the mixture is granulated by wet granulation method. Remaining quantity of (3), and (5) are added to the granules and compressed into tablets. Thus prepared tablets may further be coated with suitable coating materials, e.g. sugar.

What we claim is:

1. A compound of the general formula (I):

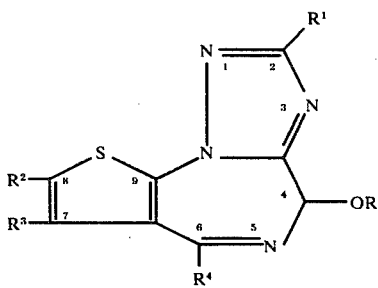

wherein $R^1$ represents a carboxyl group —$COOR^5$ in which $R^5$ is lower alkyl of 1 to 4 carbon atoms or

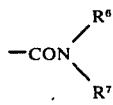

in which $R^6$ and $R^7$ represent hydrogen, straight, branched or cyclic alkyl of 1 to 6 carbon atoms; straight, branched or cyclic alkyl of 1 to 6 carbon atoms substituted by lower alkoxy of 1 to 4 carbon atoms or $R^6$ and $R^7$ taken together with the nitrogen atom to which they are attached form members selected from the group consisting of pyrrolidine, piperidine, morpholine, N-methyl piperazine, N-ethyl piperazine, N-propyl piperazine and N-(2-methoxyethyl)-piperazine each of $R^2$ and $R^3$ represent a hydrogen atom or a lower alkyl group or $R^2$ and $R^3$ taken together forming trimethylene or tetramethylene; $R^4$ is phenyl or phenyl substituted by halogen, lower alkyl, lower alkoxy, trifluoromethy, or trichloromethyl and R represents hydrogen, —$COR^8$ in which $R^8$ is alkyl of 1 to 4 carbon atoms, phenyl, tolyl, benzyl or phenethyl, or alkyl of 1 to 4 carbon atoms or its pharmaceutically acceptable acid addition salts.

2. A compound as claimed in claim 1, wherein said $R^4$ is phenyl.

3. A compound as claimed in claim 1, wherein R is hydrogen atom.

4. A compound as claimed in claim 1, wherein R is —$COR^8$ in which $R^8$ is alkyl of 1 to 4 carbon atoms, phenyl, tolyl, benzyl or phenethyl.

5. A compound as claimed in claim 4, wherein $R^8$ is phenyl, tolyl, benzyl or phenethyl.

6. A compound as claimed in claim 5, wherein $R^8$ is a lower alkyl group having 1 to 4 carbon atoms.

7. A compound as claimed in claim 1, wherein R is an alkyl group.

8. A compound as claimed in claim 7, wherein the alkyl is lower alkyl group having 1 to 4 carbon atoms.

9. A compound as claimed in claim 1, wherein $R^1$ is

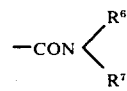

are as defined in claim 1.

10. A compound as claimed in claim 9, wherein $R^6$ and $R^7$ are both hydrogen.

11. A compound as claimed in claim 1, wherein R is hydrogen atom.

12. A compound as claimed in claim 1, wherein R is an acyl group represented by the formula —$COR^8$, wherein $R^8$ is as defined in claim 1.

13. A compound as claimed in claim 1, wherein $R^8$ represents a lower alkyl group having 1 to 4 carbon atoms.

14. A compound as claimed in claim 10, wherein R is a lower alkyl group having 1 to 4 carbon atoms.

15. A compound as claimed in claim 1, wherein $R^4$ is phenyl group.

16. A compound as claimed in claim 1, wherein $R^4$ is a phenyl group substituted at ortho-position by a halogen atom.

17. A compound as claimed in claim 16, wherein the halogen atom is chlorine.

18. A compound as claimed in claim 15, wherein $R^2$ and $R^3$ are both lower alkyl groups.

19. A compound as claimed in claim 15, wherein $R^2$ is lower alkyl group and $R^3$ is hydrogen atom.

20. A compound as claimed in claim 18, wherein the lower alkyl group represented by $R^8$ is methyl group.

21. A compound as claimed in claim 20, wherein $R^1$ is piperidinocarbonyl group.

22. A compound as claimed in claim 1, wherein $R^1$ is piperidinocarbonyl group.

23. A compound as claimed in claim 1, wherein $R^2$ and $R^3$ are both methyl groups.

24. A compound as claimed in claim 1, wherein $R^2$ is ethyl group and $R^3$ is hydrogen atom.

25. A compound as claimed in claim 1, wherein $R^4$ is a phenyl group substituted at ortho-position by a halogen atom.

26. A compound according to claim 1, namely 4-acetoxy-6-(2-chlorophenyl)-8ethyl-4H-thieno[3,2-f]-s-triazolo[1,5-a]-[1,4]diazepine-2-carboxamide.

27. A compound according to claim 1, namely 4-acetoxy-7,8-dimethyl-6-phenyl-2-piperidinocarbonyl-4H-thieno[3,2-f]-s-triazolo[1,5-a][1,4]diazepine.

28. A compound according to claim 1, namely 6-(2-chlorophenyl)-8-ethyl-4-hydroxy-4H-thieno[3,2-f]-s-triazolo-[1,5-a][1,4]diazepine-2-carboxamide.

29. A compound according to claim 1, namely 6-(2-chlorophenyl)-8-ethyl-4-methoxy-4H-thieno[3,2-f]-s-triazolo-[1,5-a][1,4]diazepine-2-carboxamide.

30. A compound according to claim 1, namely 7,8-dimethyl-4-methoxy-6-phenyl-2-piperidinocarbonyl-4H-thieno-[3,2-f]-s-triazolo[1,5-a][1,4]diazepine.

31. A pharmaceutical composition comprising about 0.1 to 100 mg. of a compound according to claim 1 or a pharmaceutically acceptable acid addition salt there of and a pharmaceutically acceptable carrier or diluent therefor.

* * * * *

UNITED STATES PATENT OFFICE
CERTIFICATE OF CORRECTION

Patent No. 4,017,620   Dated April 12, 1977

Inventor(s) Yutaka Kuwada, et al

It is certified that error appears in the above-identified patent and that said Letters Patent are hereby corrected as shown below:

Column 21, line 31: After "carboxyl group" insert a comma.

line 49: After "erazine" insert a comma.

line 53: Change "trifluoromethy" to --trifluoromethyl--.

Column 22, line 10: After " $-CON\begin{smallmatrix}R^6\\R^7\end{smallmatrix}$ " insert --, wherein each of $R^6$ and $R^7$ --.

Signed and Sealed this

Eighteenth Day of October 1977

[SEAL]

Attest:

RUTH C. MASON
Attesting Officer

LUTRELLE F. PARKER
Acting Commissioner of Patents and Trademarks